US00PP17372P3

(12) United States Plant Patent
Stemkens

(10) Patent No.: US PP17,372 P3
(45) Date of Patent: Jan. 23, 2007

(54) ***SUTERA* PLANT NAMED 'SUTCATRABL'**

(50) Latin Name: *Sutera diffusa*
Varietal Denomination: Sutcatrabl

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 187 days.

(21) Appl. No.: 11/002,472

(22) Filed: Dec. 2, 2004

(65) Prior Publication Data

US 2006/0123521 P1 Jun. 8, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—Bruce Vrana

(57) ABSTRACT

A new and distinct variety of *Sutera* plant particularly distinguished by its very big blue flowers, early to flower, thick stems and a growing habit that is spreading and trailing.

1 Drawing Sheet

Latin name of the genus and species of the plant claimed: *Sutera diffusa.*
Varietal denomination: 'Sutcatrabl'.

BACKGROUND OF THE NEW PLANT

The present invention comprises a new distinct cultivar of *Sutera,* botanically known as *Sutera diffusa.*

The new cultivar is propagated from cuttings resulting from the cross of 'B21' and 'B23'. 'B21' is a lavender blue flowering *Sutera* having a spreading, trailing habit. 'B21' is not commercially available and is not known by any synonyms. 'B23' is a white flowering *Sutera* having a larger than normal flower. 'B23' is not commercially available and is not known by any synonyms. Neither 'B21' or 'B23' has been patented.

As a result of this cross the present cultivar was created in 2000 in Enkhuizen, Netherlands and has been repeatedly asexually reproduced by cuttings in Enkhuizen, Netherlands and Sarrians, France over a three year period. The new variety reproduces true to type in successive generations of asexual reproduction and its novelty is firmly fixed.

This new *Sutera* plant is an annual in most climatical zones in the US, only in zones 9 and 10 it is a perennial plant.

'Sutcatrabl' is coming from the same cross as the variety 'Sutharis', U.S. Plant Pat. No. 15,254, from which it differs in having a dark blue color instead of a lavender color and having smaller leaves. Also, the proprietory variety 'Sutcabl' U.S. Plant application Ser. No. 11/002,510, is from the same cross. 'Sutcabl' has a lighter flower color, smaller flower size and a more compact habit than 'Sutcatrabl.'

SUMMARY OF THE INVENTION

It was found that the cultivar of the present invention:

a) Exhibits big, dark blue flowers;

b) has thick stems; and c) exhibits a spreading and trailing growth habit

DESCRIPTION OF THE DRAWING

This new *Sutera* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Sutera.* The data that define these characteristics were collected from asexual reproductions carried out in Enkhuizen, Netherlands. The plant history was taken on 15 week old plants, blossomed under natural light in a greenhouse and grown in a 11 cm container. Colour readings were taken in the greenhouse under ambient light. Colour references are primarily to The R.H.S. Colour Chart of The Royal Horticultural Society of London.

TABLE 1

DIFFERENCES BETWEEN THE NEW CULTIVAR 'SUNCATRABL', ITS PARENTS AND A SIMILAR CULTIVAR

| | 'Sutcatrabl' | 'B21' | 'B23' | 'Blue Showers' |
|---|---|---|---|---|
| Flower color | Deep Blue | Deep blue | White | Blue |
| Stem thickness | Thick | Medium | Thick | Thin |
| Plant habit | Trailing | Trailing | Compact | Trailing |
| Flower size | Big | Big | Small | Small |

The commercial name of the most resembling variety is 'Blue Showers'. The patented name of this variety is 'Bacoble' and its U.S. Plant Pat. No. is 13,181.

The plant:

*Classification.*—Botanical: *Sutera diffusa.*

*Parentage.*—Female parent: A seedling named 'B21' is one of our seedlings from our B-generation of plants bred in 1999. Pollen parent: A seedling named 'B23' is one of our seedings from our B-generation of plants bred in 1999.

*Growth habit.*—Compact.
*Plant height.*—12–17 cm.
*Spreading area of plant.*—30–50 cm.
*Growth rate.*—Rapid growing.
*Strength.*—Good.
*Branching habit.*—Short internodes and on each knot more than two appearing shoots give a plant that is more branched than normal.
*Blooming period.*—From May until November.

The stem:
*Diameter.*—2–3 mm.
*Length.*—24–44 cm.
*Shape.*—Cylindrical.
*Anthocyanin pigmentation.*—Absent.
*Color of the stem.*—135C.
*Length of internode.*—12–30 mm, depending on the light where the plant is propagated.
*Pubescence.*—Sparse.

The foliage:
*Phyllotaxis.*—Opposite.
*Number of leaves per lateral stem.*—16–36.
*Shape of blade.*—Non-symmetrical broadly ovate.
*Shape of the blade apex.*—Acute.
*Shape of the blade base.*—Non-symmetrical attenuate.
*Leaf margin.*—Dentate.
*Venation.*—Pinnate.
*Color of veins.*—Upper side: 137B. Lower side: 137D.
*Texture.*—Upper surface: Smooth, glabrous. Lower surface: Slightly pubescent.
*Length.*—8–22 mm.
*Width.*—10–23 mm.
*Thickness.*—1–2 mm.
*Depth of incision.*—Less than 1 mm.
*Color.*—Upper side: 135B. Lower side: 137C.
*Length of petiole.*—1 mm.
*Diameter of petiole.*—1 mm.
*Color of petiole.*—135B.
*Fragrance.*—Musk.

The bud:
*Peduncle length.*—12–16 mm.
*Peduncle diameter.*—1–2 mm.
*Peduncle color.*—135B.
*Peduncle angle.*—About 60 degrees from the stem.
*Bud size.*—Diameter: 2 mm. Length: 4–8 mm.
*Bud shape.*—Obovate.
*Bud color.*—85A.
*Number of buds per lateral branch.*—8–38.

The flower:
*Number of flowers per plant.*—More than 800.
*Number of flowers per lateral branch.*—8–38.
*Flower diameter.*—14–20 mm.
*Flower tube length.*—6–10 mm.
*Throat diameter, distal end.*—2.5–4 mm.
*Tube diameter, proximal end.*—1.5–2.5 mm.
*Form.*—Salverform.
*Symmetry.*—Radial symmetric.
*Type.*—Solitary, axillary.
*Color.*—Upper surface: 90C. Lower surface: From 91C in the center to N88C on the edge.
*Corolla tube.*—Cylindrical.
*Corolla tube color (tube outside).*—17D.
*Corolla throat color.*—17C.
*Overlapping of petals.*—Separate.
*No. of petals.*—5.
*Shape of the petals.*—Gamopetalous, grown together at the base of the petal, forming a corolla.
*Petal lobe.*—Length: 5–8 mm. Width: 3–5 mm. Shape: Spatulate. Apex: Rounded. Margin: Entire. Texture: Smooth.
*Shape of sepals.*—Gamopetalous, grown together at the base of the sepal.
*Sepals.*—Color both surfaces: 137C to 137B. Number: 5. Shape: Narrow, linear. Length: 2 mm. Width: 1 mm. Apex: Acute. Margin: Entire.
*Calyx.*—Length: 2 mm. Diameter: 2 mm. Shape: Erect calyx.
*Texture of the calyx.*—Upper surface: Pubescent. Lower surface: Pubescent.
*Anthocyanin pigmentation of calyx limb.*—Absent.
*Flower fragrance.*—No fragrance detected.
*Lastingness of one flower.*—Flowers stay open 8–10 days.
*Natural flowering season.*—Year round in greenhouse environment and Spring through Autumn in outdoor garden.

Reproductive organs:
*Number of reproductive organs.*—1 pistil, 4 stamens.
*Anther shape.*—Linear.
*Anther length.*—1 mm.
*Anther color.*—16C.
*Pollen production.*—Very low.
*Pollen color.*—13B.
*Stigma shape.*—Rounded.
*Stigma color.*—138D.
*Stamen color.*—13B.
*Stamen arrangement.*—Didynamous.
*Stamen type.*—Basifixed.
*Dehiscence of stamens.*—Extrorse.
*Ovary position.*—Ovary superior, flower hypogynous.
*Ovary color.*—128D.
*Style shape.*—Style terete.
*Style length.*—5 mm.
*Pistil length.*—8 mm.

The fruit and the seeds: No fruit development nor seed set has been observed.

Roots:
*Type of roots.*—Fibrous and fine, color 155A.

Disease/pest resistance: Plants of the new *Sutera* has been noted to be resistant to pathogens or pests common to *Sutera.*

Temperature tolerance: Plants of the new *Sutera* have been observed to tolerate temperatures from 4 to 32 degrees C.

Propagation: Propagation is done by axillary cuttings. Tips of stems are used, which take 6 days to initiate roots and 12 days to develop roots.

What is claimed is:

1. A new and distinct variety of *Sutera* plant named 'Sutcatrabl', substantially as illustrated and described herein.

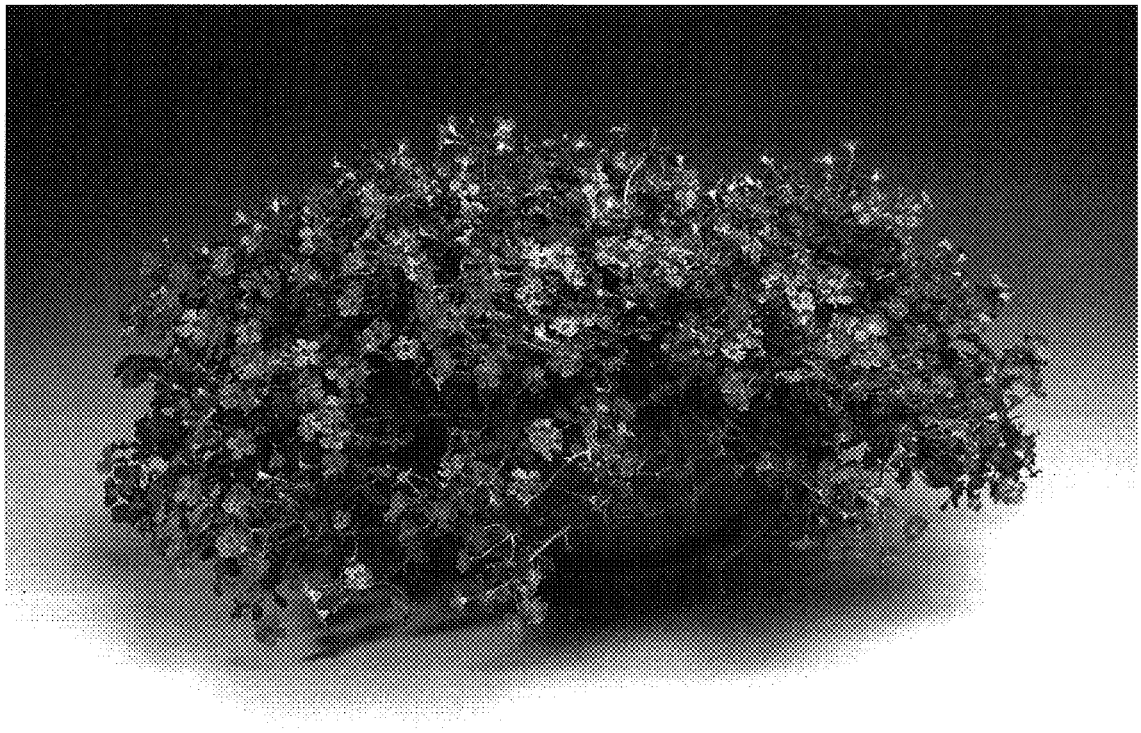

* * * * *